US00PP28291P3

(12) United States Plant Patent
Danziger

(10) Patent No.: US PP28,291 P3
(45) Date of Patent: Aug. 15, 2017

(54) ***PETUNIA* PLANT NAMED 'DRAYSALMON'**

(50) Latin Name: *Petunia sensu wijsman*
Varietal Denomination: Draysalmon

(71) Applicant: Gavriel Danziger, Mishmar Hashiva (IL)

(72) Inventor: Gavriel Danziger, Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 135 days.

(21) Appl. No.: 14/545,655

(22) Filed: Jun. 2, 2015

(65) Prior Publication Data

US 2016/0360685 P1 Dec. 8, 2016

(51) Int. Cl.
*A01H 5/02* (2006.01)

(52) U.S. Cl.
USPC ..... Plt./356.13

(58) Field of Classification Search
USPC ..... Plt./263.1, 356.1, 356.13
See application file for complete search history.

(56) References Cited

PUBLICATIONS

Greenhouse Management: Variety notebook; May 5, 2014. http://www.greenhousemag.com/article/gm0514-new-flower-varieties/. 3 pages.*

* cited by examiner

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Petunia* cultivar named 'DRAYSALMON' is disclosed, characterized by mounded, ball-shaped growth habit, very well branched plant form, medium vigor and an abundance of large light orange flowers with white centers. The new variety is a *Petunia*, normally produced as an outdoor garden or container plant.

2 Drawing Sheets

Figure 1:
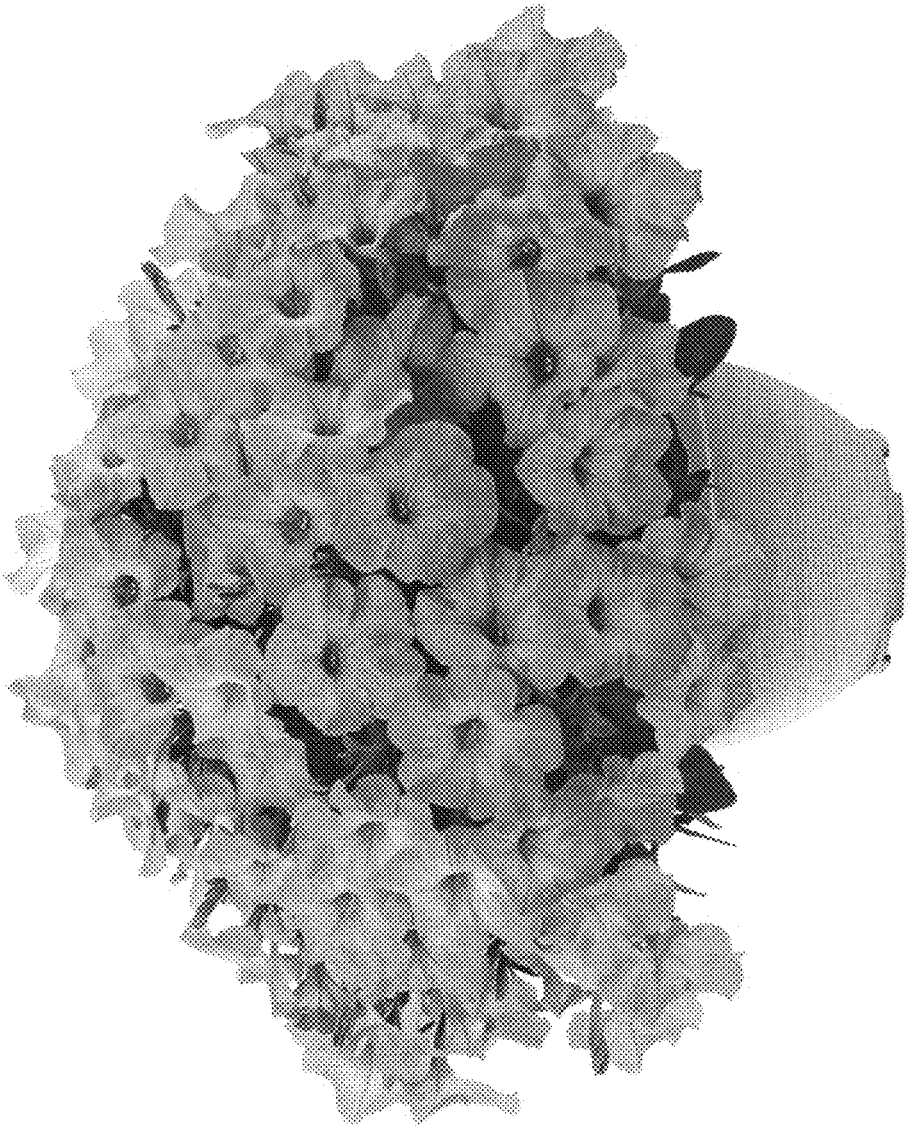

Latin name of the genus and species: *Petunia sensu wijsman.*

Variety denomination: 'DRAYSALMON'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during October of 2011.

The seed parent is the, unpatented, proprietary variety referred to as *Petunia* cv. 11-4727'. The pollen parent is the unpatented, propriety variety referred to as *Petunia* 'cv. 11-4904'. The new variety was discovered in May of 2012 by the inventor in a group of seedlings resulting from the 2011 crossing, in a research greenhouse in Moshav Mishmar Hashiva, Israel.

Asexual reproduction of the new cultivar was first performed by terminal vegetative cuttings. This first propagation occurred at a research greenhouse in Moshav Mishmar Hashiva, Israel in May of 2012 and has shown that the unique features of this cultivar are stable and reproduced true to type in more than 25 successive generations.

SUMMARY OF THE INVENTION

The cultivar 'DRAYSALMON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DRAYSALMON' These characteristics in combination distinguish 'DRAYSALMON' as a new and distinct *Petunia* cultivar:

1. Very branched with medium vigor.
2. Mounded, ball-shaped growth habit.
3. Large flower size.
4. Abundant flowering.
5. Unique light orange flower color with a white center.

Plants of the new cultivar 'DRAYSALMON' are similar to plants of the seed parent, in most horticultural characteristics, however, plants of the new cultivar 'DRAYSALMON' differ in the following;

1. Mounded ball-shaped growth habit, whereas the seed parent has a semi-upright growth habit.
2. The new variety has slightly smaller flowers.
3. Flowers color is orange with a white center, while the seed parent flower is yellow.
4. The new variety produces more flowers per plant.
5. The new variety produces more branches per plant.

Plants of the new cultivar 'DRAYSALMON' are similar to plants of the pollen parent, in most horticultural characteristics, however, plants of the new cultivar 'DRAYSALMON' differ in the following;

1. Mounded ball-shaped growth habit, whereas the pollen parent has a mounded, but not as round, ball-shaped growth habit.
2. The new variety produces larger flowers.

3. Flowers color of the new variety is orange with a white center, whereas the flower color of the pollen parent is red.
4. The parent variety produces more flowers per plant.
5. The new variety is a larger plant with greater vigor.

COMMERCIAL COMPARISON

Plants of the new cultivar 'DRAYSALMON' are comparable to the patented commercial variety *Petunia* 'DANRAY1', U.S. Plant Pat. No. 20,974. The two *Petunia* varieties are similar in most horticultural characteristics; however, the new variety 'DRAYSALMON' differs in the following:

1. Flowers of the comparator are softer and more undulating than flowers of the new variety.
2. Flower color of this comparator is white, whereas the new variety has orange flowers with a white center.
3. The comparator plant is highly vigorous, whereas the new variety has medium vigor.
4. Branches are longer, whereas the branches of the new variety are shorter.

Plants of the new cultivar 'DRAYSALMON' can also be comparable to the commercial variety *Petunia* 'DANRAY2' U.S. Plant Pat. No. 20,966. The two *Petunia* varieties are similar in most horticultural characteristics; however, the new variety 'DRAYSALMON' differs in the following:

1. Foliage size is larger than the foliage of the new variety.
2. Flower color is dark pink, while the new variety has orange flowers with a white center
3. The comparator plant is highly vigorous, whereas the new variety has medium vigor.
4. Average branch length of the comparator is longer than branches of the new variety.

BRIEF DESCRIPTION OF THE PHOTOGRAPHS

The accompanying photograph in FIG. 1 illustrates in full color a typical plant of 'DRAYSALMON' grown in a nursery, in a 13 cm pot. Age of the plant photographed is approximately 90 days from a rooted cutting.

Figure 2:
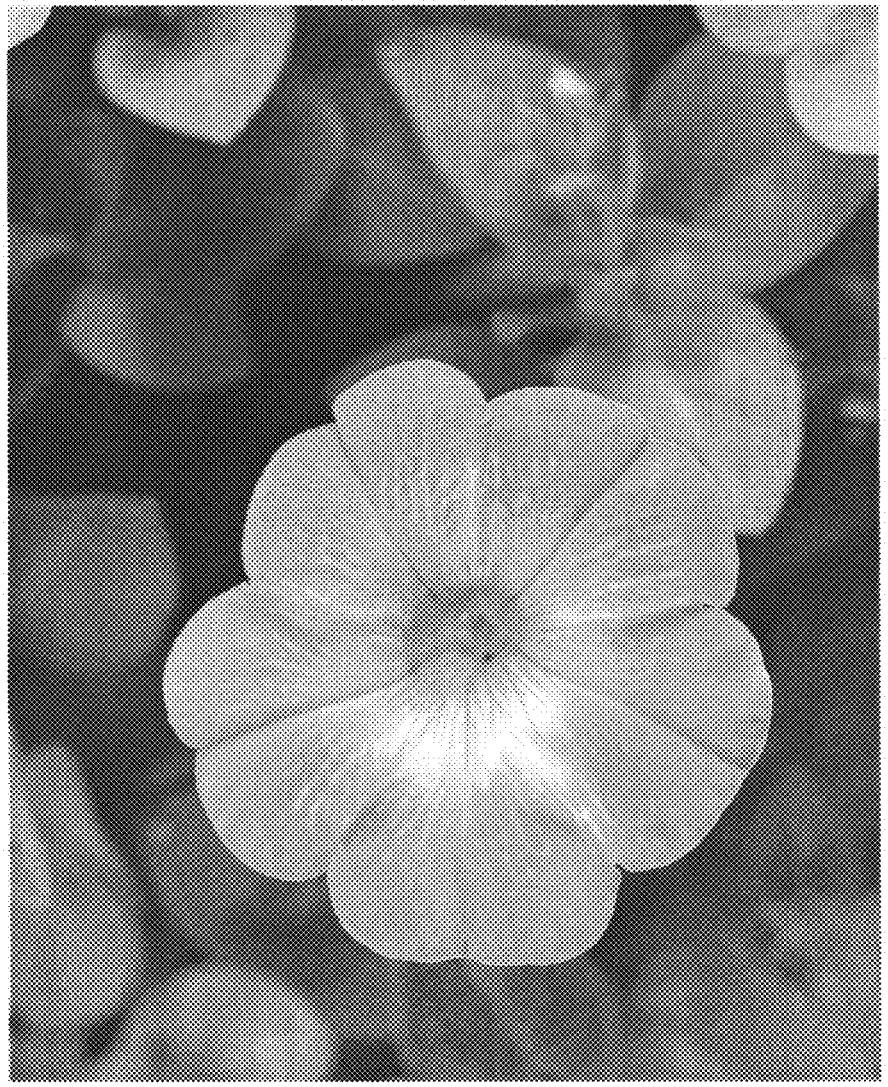

FIG. 2 illustrates a close up of a flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DRAYSALMON' plants grown outdoors and in greenhouse during the Spring, Summer and Autumn, in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia* 'DRAYSALMON'.

PROPAGATION

Type of propagation typically used: Cutting.
Time to initiate roots: 10-14 days.
Root description: Fibrous.

PLANT

Age of plant described: Approximately 60 days from a rooted cutting.
Pot size of plant described: 13 cm.
Growth habit: Mounded.
Height: Approximately 23 cm.
Plant spread: About 55 cm.
Growth rate: Medium.
Branching characteristics: Very well branched.
Characteristics of primary lateral branches:
*Quantity of primary lateral branches.*—8.
*Length of primary lateral branches.*—About 25 cm.
*Form.*—Cylindrical.
*Diameter.*—About 0.3 cm.
*Color.*—RHS Yellow-Green 146B.
*Texture.*—Pubescent.
*Strength.*—Strong and flexible.
Internode length: Average 2.0 cm.

FOLIAGE

Leaf:
*Arrangement.*—Opposite.
*Quantity.*—Approximately 22 per branch.
*Average length.*—6.5 cm.
*Average width.*—3.0 cm.
*Shape of blade.*—Elliptic.
*Apex.*—Acute.
*Base.*—Tapered.
*Margin.*—Entire.
*Texture of top surface.*—Velvety.
*Texture of lower surface.*—Velvety.
*Color.*—Young foliage upper side: RHS Yellow-Green 146 A. Young foliage under side: RHS Yellow-Green 146 B. Mature foliage upper side: RHS Yellow-Green 146 A. Mature foliage under side: RHS Yellow-Green 146 B.
*Venation.*—Type: Pinnate. Venation color upper side: RHS Yellow-Green 146 C. Venation color under side: RHS Yellow-Green 146 D.
*Petiole.*—Length: 1.0 cm. Diameter: 0.4 cm. Color: RHS Yellow-Green 146 B. Texture: Velvety.

FLOWER

Natural flowering season: Spring, Summer, and Autumn in Mishmar Hashiva, Israel.
Days to flowering from rooted cutting: About 30 days.
Inflorescence and flower type and habit: Axillary, single flower, salverform shape, erect habit.
Rate of flower opening: 2 to 3 days from bud to fully opened flower.
Flower longevity on plant: 3-6 days.
Approximate quantity of flowers per plant: About 80.
Persistent or self-cleaning: Self-cleaning.
Bud:
*Shape.*—Tubular.
*Length.*—5.0 cm.
*Diameter.*—About 0.8 cm.
*Color.*—RHS Green-Yellow 1B.
Flower size:
*Diameter.*—About 6.5 cm.
*Flower tube length.*—About 3.0 cm.

*Flower tube diameter at distal end.*—1.0 cm.
*Flower tube diameter at proximal end.*—0.2 cm.

Petals:
*Length from throat.*—About 3 cm.
*Width.*—About 3.5 cm.
*Quantity.*—5.
*Texture.*—Velvety.
*Apex.*—Blunt.
*Base.*—Fused.
*Margin.*—Wavy.

Color:
*When opening.*—Upper surface: Near RHS Orange-Red 33B. Center RHS Yellow-White 158B. Lower surface: Near RHS Orange 29C.
*Fully opened.*—Upper surface: Near RHS Orange-Red 32B with center near RHS Yellow-White 158C. Lower surface: Near RHS Orange 29C. Flower throat (inside): Near RHS Yellow-Green 152B. Flower throat, vein: Near RHS Yellow-Green 146C. Flower tube (outside): Near RHS Yellow-Green 144C. Flower tube, vein: Near RHS Yellow-Green 144A.
*Fading.*—Petals fading to: Near RHS Red 39B.
*Calyx/sepals.*—Quantity per flower: 5. Shape: Linear. Length: about 1.8 cm. Width: about 0.3 cm. Apex: Rounded. Base: Fused. Margin: Entire. Texture: velvety, upper and lower surfaces. Color: Upper Surface: RHS Yellow-Green 146 A. Lower Surface: RHS Yellow-Green 146 B.

Peduncle: Not Present.

Pedicel:
*Length.*—About 4 cm.
*Diameter.*—About 0.2 cm.
*Color.*—RHS Yellow-Green 146 B.
*Orientation.*—Straight, average angle of attachment 45 degrees Fragrance: None. .

REPRODUCTIVE ORGANS

Stamens:
*Number.*—5.
*Filament length.*—About 1.8 cm.

Anthers:
*Length.*—About 0.1 cm.
*Shape.*—Rounded.
*Color.*—RHS Yellow-Orange 18 B.
*Pollen.*—Color: RHS Yellow-Orange 16 D. Quantity: Abundant.

Pistil:
*Number.*—1.
*Length.*—About 2.8 cm.
*Style.*—Length: about 2.3 cm. Color: RHS Yellow-Green 144C.
*Stigma.*—Shape: Rounded. Color: RHS Yellow-Green 144B. Ovary Color: RHS Yellow-Green 144A.

OTHER CHARACTERISTICS

Seeds and fruits: About 50 Black, rounded seeds of about 0.5 mm diameter, per one brown, conical capsule. Seed color close to 200A, capsule color close to 200D.

Disease/pest resistance: Neither resistance nor susceptibility to the normal diseases and pests of *Petunia* have been observed. Typical well known diseases include: *Botrytis cineria, Fusarium, Pythium, Phytophthora,* and *Rhizoctonia* species. Typical well known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'DRAYSALMON' as herein illustrated and described.

* * * * *